United States Patent
Simons et al.

[19]

[11] Patent Number: 5,871,494
[45] Date of Patent: Feb. 16, 1999

[54] REPRODUCIBLE LANCING FOR SAMPLING BLOOD

[75] Inventors: Tad Decatur Simons, Palo Alto; Michael Greenstein, Los Altos; Dominique Freeman, Cabrillo Hwy.; Leslie Anne Leonard, Portolla Valley; David A. King, Menlo Park; Paul Lum, Los Altos, all of Calif.

[73] Assignee: Hewlett-Packard Company, Palo Alto, Calif.

[21] Appl. No.: 985,303

[22] Filed: Dec. 4, 1997

[51] Int. Cl.$^6$ ..................................................... A61B 17/14
[52] U.S. Cl. ........................ 606/181; 606/181; 606/182; 606/183; 606/184; 606/185; 606/186; 604/137; 604/157
[58] Field of Search ..................................... 606/181, 182, 606/183, 184, 185, 186; 604/137, 187

[56] References Cited

U.S. PATENT DOCUMENTS

| | | |
|---|---|---|
| 2,061 | 4/1841 | Osdel . |
| 55,620 | 6/1866 | Capewell . |
| 1,135,465 | 4/1915 | Pollock . |
| 3,030,959 | 4/1962 | Grunert ................................. 128/329 |
| 3,358,689 | 12/1967 | Higgins .................................. 128/329 |
| 4,139,011 | 2/1979 | Benoit et al. .......................... 128/329 |
| 4,203,446 | 5/1980 | Hofert et al. .......................... 128/329 |
| 4,207,870 | 6/1980 | Eldridge ................................ 128/766 |
| 4,230,118 | 10/1980 | Holman et al. ......................... 128/314 |
| 4,442,836 | 4/1984 | Meinecke et al. ...................... 128/314 |
| 4,449,529 | 5/1984 | Burns et al. ........................... 128/314 |
| 4,469,110 | 9/1984 | Slama .................................... 128/770 |
| 4,535,769 | 8/1985 | Burns ..................................... 128/314 |
| 4,577,630 | 3/1986 | Nitzsche et al. ....................... 128/314 |
| 4,712,548 | 12/1987 | Enstrom ................................. 128/314 |
| 4,895,147 | 1/1990 | Bodicky et al. ........................ 606/182 |
| 5,133,730 | 7/1992 | Biro et al. .............................. 606/182 |
| 5,196,025 | 3/1993 | Ranalletta et al. ..................... 606/182 |
| 5,318,583 | 6/1994 | Rabenau et al. ........................ 606/182 |
| 5,318,584 | 6/1994 | Lange et al. ............................ 606/181 |
| 5,366,470 | 11/1994 | Ramel et al. ........................... 606/183 |
| 5,510,266 | 4/1996 | Bonner et al. ............................ 436/43 |
| 5,569,287 | 10/1996 | Tezuka et al. .......................... 606/182 |
| 5,571,132 | 11/1996 | Mawhirt et al. ........................ 606/167 |
| 5,613,978 | 3/1997 | Harding ................................... 606/181 |
| 5,632,410 | 5/1997 | Moulton et al. .......................... 221/79 |

FOREIGN PATENT DOCUMENTS

0630609A2  12/1994  European Pat. Off. .......... A61B 5/14

OTHER PUBLICATIONS

Softclix ®, "Lancet Device from the Makers of Accu–Chek ® Systems", (Product), PP. (3 pages), Becton Dickinson & Co., Franklin Lakes, New Jersey.
One Touch ® Profile™ "Diabetes Tracking System", Owner's Booklet, (Product), pp. 31–33, LifeScan Inc.
Glucometer Elite ®, "Diabetes Care System", User's Guide, (Product), PP. (3 pages), Miles Inc. Elkhart, IN.

*Primary Examiner*—Michael Buiz
*Assistant Examiner*—Vy Quang Bui
*Attorney, Agent, or Firm*—Philip S. Yip

[57] ABSTRACT

A blood analysis apparatus for obtaining blood for analysis from the skin of a patient with a controlled degree of lancing. The apparatus including a cartridge and a driver. The cartridge includes a cartridge case and a lancet. The lancet has a tip and is housed in the cartridge case. The lancet can be driven to extend the tip outside the cartridge case through an opening for lancing the skin of the patient to yield blood. The driver drives the lancet to move the tip distally to lance the skin. The driver is triggerable by the skin which is to be lanced exerting a force exceeding a preset amount against the triggering mechanism of the apparatus, to drive the lancet toward the skin.

21 Claims, 11 Drawing Sheets

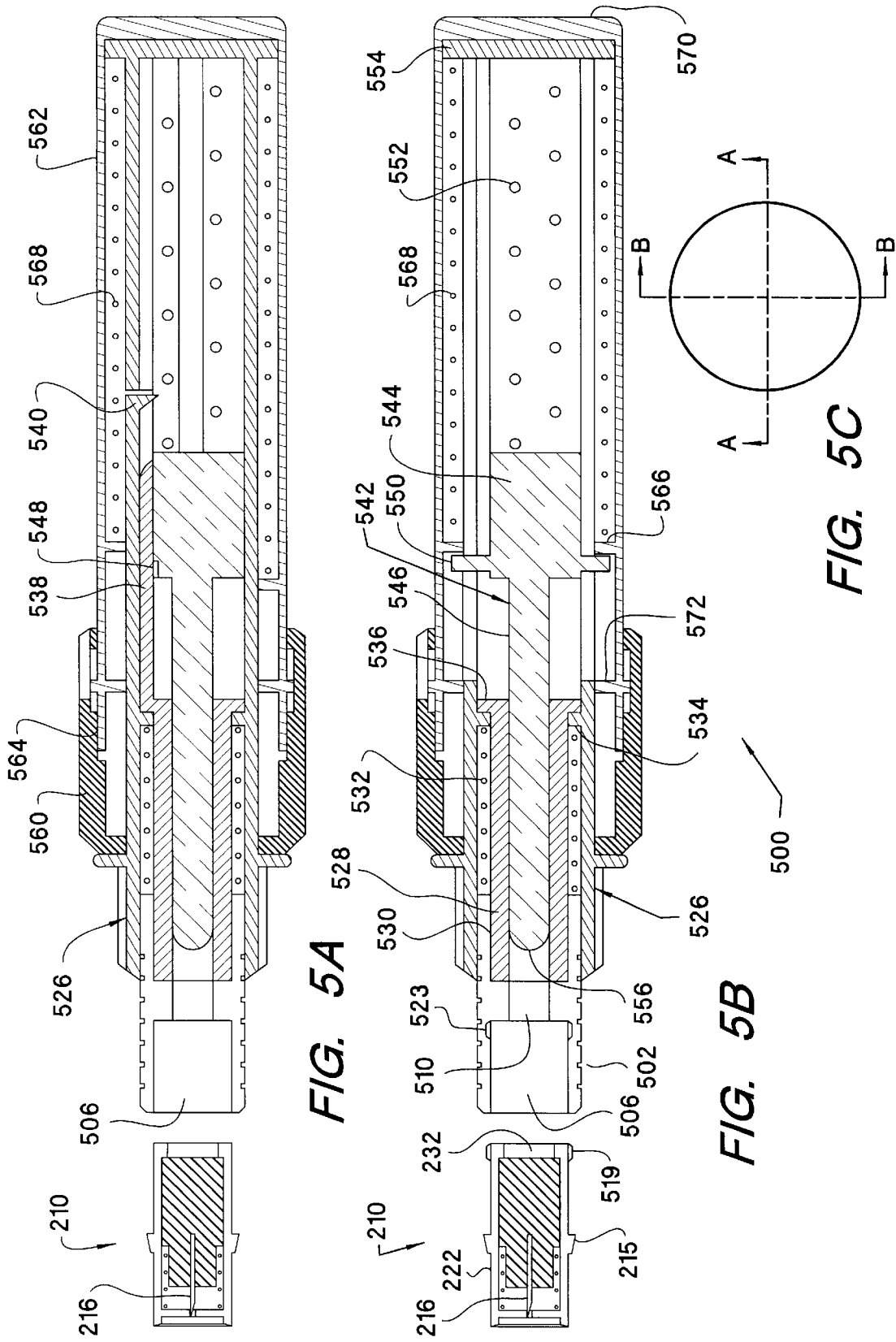

REPRODUCIBLE LANCING FOR SAMPLING BLOOD

FIELD OF THE INVENTION

The present invention relates to techniques for obtaining and analyzing blood samples, and more particularly to techniques for lancing the skin with a controlled force for obtaining and analyzing blood samples in a convenient manner.

BACKGROUND

The analysis and quantification of blood components is an important diagnostic tool for better understanding the physical condition of a patient. Since adequate noninvasive blood analysis technology is not currently available, blood samples still need to be obtained by invasive methods from a great number of patients every day and analyzed. A well known example of such needs is self monitoring of glucose levels by a diabetic individual, e.g., performed at home. Many products for self monitoring of blood glucose levels are available commercially. Upon doctors' recommendations and using such products, patients typically measure blood glucose level several (3–5) times a day as a way to monitor their success in controlling blood sugar levels. For many diabetics, the failure to test blood glucose regularly may result in damage to tissues and organs, such as kidney failure, blindness, hypertension, and other serious complications. Nevertheless, many diabetics do not measure their blood glucose regularly. One important reason is that the existing monitoring products may be complicated, inconvenient, and painful, requiring a pinprick every time a measurement is made. Furthermore, these products require some skill, dexterity, and discipline to obtain useful measurements.

Today, a diabetic patient who needs to monitor and control blood glucose levels typically carries the following paraphernalia: (1) a supply of disposable lancets, (2) a reusable lancing device which accepts the lancets, (3) an electronic glucose meter (glucometer), (4) a supply of disposable glucose test strips for the meter, and (5) tools for insulin injection (insulin, disposable hypodermic needles, and a syringe). These items may be carried in the form of a kit, which may also contain (6) a variety of control and calibration strips to assure the accuracy of the meter and the measurement. Examples of devices for monitoring blood glucose include GLUCOMETER ELITE glucose meter, Miles Inc. Elkhart, Ind., and ONE TOUCH PROFILE glucose meter, Lifescan Inc., Milpitas, Calif.

Using a typical glucose meter and lancing device, the sampling and measurement process is generally as follows. First, the user prepares the meter for use by removing a test strip from a protective wrapper or vial and inserting the test strip in the meter. This simple process requires some dexterity, since the test strips are very small, flexible, and can be damaged by accidentally touching the active sensing region. The glucose meter may confirm the proper placement of the test strip and indicate that it is prepared for a sample. Some glucose meters also may require a calibration or reference step at this time. Next, the patient cleans his finger when he intends to use the lancet—the finger is the preferred place for routine sampling, because it is an easily accessible place for most people. The user prepares the lancing device by (1) removing a cover from the lancing device, (2) placing a disposable lancet in the lancing device, (3) removing a protective shield from the sharp lancet tip, (4) replacing the cover, and (5) setting a spring-like mechanism in the lancing device which provides the force to drive the lancet into the skin. These steps may happen simultaneously, e.g., typical lancing devices set their spring mechanisms when one installs the lancet. The user then places the lancing device on the finger. (The density of nerve endings decreases toward the lateral edges of the fingertips; thus, slightly lateral locations are preferred to the fingertips.) After positioning the lancing device on the finger, the user presses a button or switch on the device to release the lancet. The spring drives the lancet forward, creating a small wound.

After lancing, a small droplet of blood may appear spontaneously at the lancing site, usually 2–20 $\mu$l in volume. If no blood sample appears spontaneously, the patient may "milk" the finger by massaging or squeezing it slightly and thereby promoting blood flow from the wound. In either case the user examines the droplet of blood, judges by eye and experience whether the size of the sample is adequate for the chosen test strip (different test strips require different sample volumes). If adequate, the user quickly places the blood sample on a test strip (held in the glucose meter) according to manufacturer's instructions. Typically, the user inverts the finger to create a pendant drop and touches the drop (not the finger) to an active region on the test strip that absorbs the blood. The action is difficult because inverting the finger over the test strip occludes the view of both the drop and the active region of the test strip. Furthermore, it is difficult to control the separation between the finger and the test strip which may be only a millimeter. Certain types of strip may require blotting and rubbing in a particular way. Another type of test strip draws the sample into the active region by capillary action. With this type, the user brings the sample in contact with a small opening on the test strip, and capillary action draws the sample volume into the test strip. Both types of strips (absorbent blots and capillaries) require that adequate sample volumes of blood exist on the finger before transferring the sample to the strip. One cannot apply more drops after the first application. This is because the principle of glucose measurement methods using current glucose meters depends on the rate of change in a chemical reaction, and the addition of additional sample confounds that rate and thus the calculation of glucose concentration. For convenience to the patient (user), it is desirable to have the entire droplet wick away from the finger onto the test strip, leaving the finger mostly free of blood. This is easier to accomplish with the capillary-fill test strips. The GLUCOMETER ELITE device has capillary-fill type test strips which require a few microliters of sample, only some fraction of which contacts the active sensor region.

After blood has been transferred to the test strip, the glucose meter then measures the blood glucose concentration (typically by chemical reaction of glucose with reagents on the test strip). Such blood glucose measurements permit the diabetic to manage his glucose levels, whether that be to inject a corresponding dose of insulin (generally Type I diabetic) or using a protocol established with his physician to modify his diet and exercise (Type I or Type II diabetic). Used lancets and test strips are removed and discarded (or kept for subsequent disposal in a hazardous waste container kept elsewhere). Any extra blood is cleaned from the equipment and the wound site, and all pieces of apparatus are stored for future use. The entire process usually takes a few minutes.

With the currently available blood glucose monitoring technology, a new lancet and test strip are used every time. The lancet and test strip are separate items, often purchased from different manufacturers. Furthermore, both are protected by a package or a protective shield, which must be removed before use, adding the requirement for dexterity. Because both are exposed to blood (considered a bio-hazard) they require careful or special disposal.

Each lancet prick causes pain. Among other considerations, pain from the lancet corresponds to the size of the wound, for a given location on the finger. A small lancet wound, which may cause less pain, may not provide enough blood for a sample, while a large wound may produce considerable pain and may clot slowly, causing great inconvenience to the user, who must take great care not to smear the leaking blood everywhere—clothes, work surfaces, glucometer, etc.—for some time thereafter.

From the above, it is clear that the conventional technique for blood sampling and analysis requires dexterity. Dexterity is required to load strips in a glucometer (unwrapping and inserting), as well as for positioning a small droplet onto the sensor surface of a test strip. Sample droplets are a few millimeters across and must be placed on similarly sized area of the test strip. This can be especially difficult for a weak, chronic or elderly diabetic patient, whose motions may be unsteady, vision compromised, or judgment impaired. Thus, the above prior systems are inconvenient and unpleasant to use. These shortcomings reduce the level of compliance of patients who need to perform these measurements assiduously.

In the current designs of the lancing devices, much variation in penetration depth of the lancets can result due to different placement and handling of the devices by the user. For example, if the user presses a lancing device firmly against the skin, the skin is taut and the lancet penetrates deeply and therefore more painfully. If the user holds the lancing device against the skin lightly, the skin is loose, more elastic, and more flexible than a taut skin. In this case, when the lancet moves against the skin it first creates a shallow depression before penetrating the skin, thus resulting in a shallow wound. Such a problem of uncertainty in lancing is especially pronounced in individuals whose dexterity has been impaired by chronic illnesses. With existing lancing tools, the lancing depth can vary from almost nil (therefore no wound and no blood sample) to very deep (~1 mm deep wound, spontaneously flowing blood, and considerable pain). Therefore, it is desirable to devise techniques of blood extraction and measurement that are easy to administer. What is needed are improved devices and methods for sampling and analyzing blood that require less mental concentration, less exertion, and less dexterity. What is especially needed is a lancing device with which a patient can more easily control the lancing force and lancing depth.

SUMMARY

This invention provides techniques for extracting a sample of human blood for the measurement of one or more of its constituents, such as might be used for routine monitoring of a chronic condition such as diabetes mellitus. The techniques of the present invention simplify the extraction and transfer of the blood sample, and reduce the inconvenience of the process. The techniques can be advantageously used in, for example, blood glucose monitoring as explained above.

In one aspect of the present invention, an apparatus for lancing with adjustable lancing characteristics that can result in reproducible lancing wounds is provided. The apparatus has a cartridge and a driver. The cartridge includes a cartridge case that has a lancing opening and a lancet with a tip. The lancet is operatively connected to the cartridge case to allow the lancet, when driven by the driver, to protrude through the lancing opening. The driver is triggerable by pressing the lancing device against the skin which is to be lanced, thereby exerting a force against the apparatus. When the exerted force exceeds a preset amount (preload force), the driver is triggered to drive the lancet through the lancing opening.

In an embodiment of the blood sampling apparatus, the preload force is adjustable to allow the user to customize the lancing force to provide an adequate blood sample and to minimize pain. In an embodiment, the apparatus can be adjusted to vary the depth of the lancing wound. Therefore, using the apparatus of the present invention, the user can have significant control of the force and depth of lancing, thereby finding the ideal combination that enables him to collect adequate blood without undue amount of suffering. Such an adjustable lancing technique results in reproducible lancing even for a user who has impair dexterity or eyesight because the lancing apparatus is triggered when a controlled amount of force is exceeded.

Furthermore, in the present invention, a preferred embodiment of the apparatus can be a complete system with the cartridge, the driver, as well as spare cartridges in a unit. Also, the whole process of sampling and analyzing blood can be accomplished without taking components from different packages and assembling them together every time blood sampling and analysis are performed. Once assembled, the components such as the cartridges, container enclosing the cartridges, and glucometer can remain together for multiple use, thus significantly simplifying the process of lancing, blood sampling, and analysis. Using the blood sampling and analysis devices of the present invention, unlike prior procedures, the long list of steps required is significantly reduced.

BRIEF DESCRIPTION OF THE DRAWINGS

The following figures are included to better illustrate the embodiments of the apparatus and technique of the present invention. In these figures, like numerals represent like features in the several views.

FIG. 5A shows a sectional view of a blood sampling device suitable for used with a bar-shaped test cartridge in accordance with the present invention, FIG. 5B shows a sectional view of the blood sampling device of FIG. 5A taken on a sectional plane of at a right angle thereto.

FIG. 5C shows a schematic cross-section relating the sectional views of FIGS. 5A and 5B.

DETAILED DESCRIPTION

In one aspect of the invention, the present invention provides an apparatus—a lancing device—that has a driving mechanism to drive the lancets in cartridges to lance the skin of patient with reproducible lancing force and depth in multiple lancing episodes. A lancing device of the present invention facilitates sampling blood safely, analyzing the blood sample conveniently, and disposing of the lancet safely. In some preferred embodiments, using the lancing device, a patient can perform these sampling and analysis activities without touching the lancet or cartridge by hand.

Cartridges

The lancing device for driving cartridges can be designed and made for a wide variety of cartridges in accordance with the present invention. For example, embodiments of cartridges that can be used with the lancing devices of the present invention is disclosed in copending U.S. Patent Application entitled "Lancet Cartridge for Sampling Blood," Docket No. 10971750-1, filed on the same day and commonly assigned to the same assignee as the present application. Said copending application is incorporated by reference in its entirety herein. It is to be understood that although test cartridges with analytical regions are described in more detail herein, the present invention is also applicable with cartridges that do not have an analytical region, such as a cartridge having a chamber for storing blood after sampling.

An example of a cartridge suitable for use in the present invention includes a lancet, a cartridge case with an opening through which the lancet can protrude, and a test area associated with the housing for analysis of blood. The lancet is mounted in the cartridge case in such a manner that (1) it can move with respect to the cartridge case and extend through the opening when forced by a separate actuator, and (2) when no actuating force acts on the cartridge, the lancet has a natural resting position entirely inside the cartridge case. Analysis can be done in the test area. An alternative is that a chamber can be used to store blood to be transferred to a separate analytical area from the test area. Further, although lancing with test cartridges are described in detail herein as illustrative examples, it is to be understood that the lancing apparatuses of the present invention may be applicable for other types of cartridges, including test cartridges with analysis capabilities, and "storage cartridges" in which blood is stored after sampling without analytical function. Also, other variations of the lancing apparatuses of the present invention can be made for use with other cartridges described herein.

FLAT CARTRIDGES

Figure 1A:
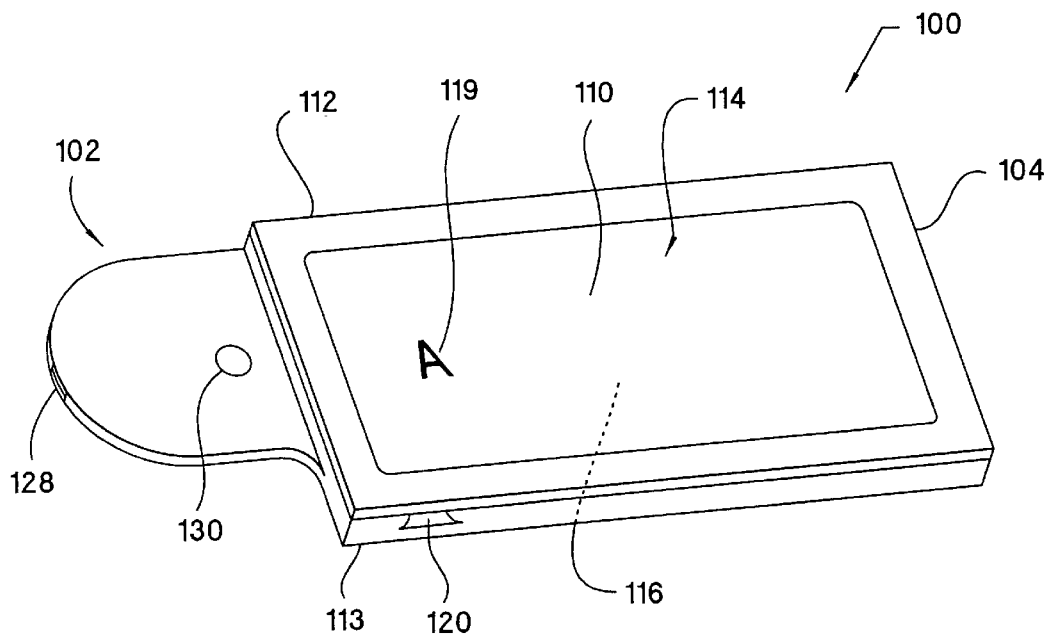
FIG. 1A shows an isometric view of an embodiment of the flat type of test cartridge of the present invention.
Figure 1B:
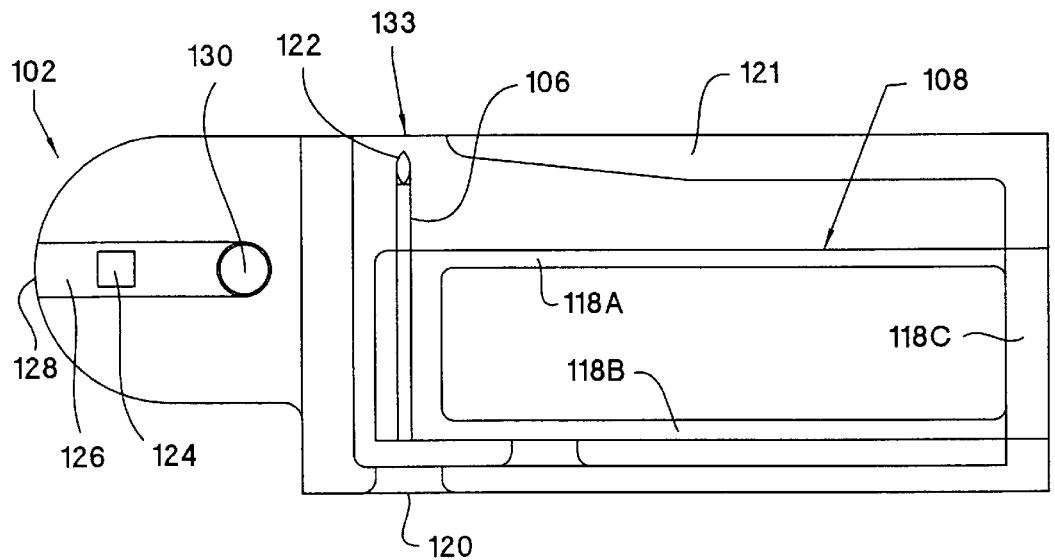
FIG. 1B shows a plan view of the test cartridge of FIG. 1A.

FIG. 1A shows an isometric view and FIG. 1B shows a plan view of an embodiment of a cartridge—a test cartridge having an analytical region and that can be included in a lancing apparatus of the present invention. The test cartridge of FIG. 1A and FIG. 1B has a generally flat appearance, thus allowing many cartridges to be stacked together for storage in a container. However, it is to be understood that other non-flat-shaped cartridges can also be used, so long as they can be stacked. For example, the cartridge can have two opposite surfaces each having a cross section that is curved, wavy, etc. to match the other surface. A test portion 102 protrudes from one side of the test cartridge 100. The test cartridge 100 can include a material for analysis of blood (see infra). The device 100 is referred to as a "test cartridge" because strips for analysis of blood in prior glucose meters are call "test strips" in the technical field. The test cartridge 100 has a cartridge case 104 integrally connected with the test area 102. A lancet 106 is connected to a cantilever lancet frame 108. The side of the cantilever lancet frame 108 remote to the lancet 106 is affixed to the cartridge case 104 whereas the side of the cantilever frame 108 near the lancet 106 is not affixed to the cartridge case 104. Thus, the lancet is operatively connected in the cartridge case 104 for movement. A covering 110 which has an absorbent material (for absorbing residual blood from the wound after lancing and testing) covers a surface (preferably the top surface) of the cartridge case 104. As used herein, the term "top surface" when used in connection with the generally flat cartridge refers to the surface that is exposed for the most convenient access when the cartridge is installed in association with a driver for lancing. Preferably, the top surface will face the same direction as displays of a glucometer when the cartridge is loaded (or deployed) in the glucometer. Preferably, the cartridge case has a top face 114 on a top plate 112 and a bottom face 116 on a bottom plate 113 that are generally flat such that cartridges of this kind can be stacked one on top of another, and such that the covering material 110 can be conveniently used for wiping blood from the skin after lancing.

In this embodiment, as shown in FIG. 1B, the lancet 106 is mounted on a two-armed cantilever frame 108, the arms 118A, 118B of the cantilever frame 108 being about 20 mm long. A separate mechanism (e.g., an actuator rod not shown in the figures) inserted through a push port (or access hole) 120 can push the lancet 106 forward by acting against the part of the cantilever frame near the blunt end of the lancet 106. The lancet 106 at its distal end remote from the blunt end has a sharp tip 122 for penetrating the skin. As used herein, the term "distal" refers to a location or direction towards the skin to be lanced. The term "proximal" refers to a location or direction that is opposite to "distal," near to the hand that is handling the lancing device. The cantilever structure causes the lancet 106 to move in a generally straight direction (parallel to the lancet axis) with negligible curving or sideways motion, in order to pierce the skin with minimal tearing. In an at-rest state the lancet 106 resides about 0.5 mm proximal of the outside surface of the cartridge to prevent unintended injuries to the user. The lancet 106 is preferably 0.35 mm in diameter or smaller in order to not inflict a large wound.

When pushed, i.e., actuated, the lancet 106 extends through the cartridge wall through an exit port 133. The lancet 106 will extend out of the distal side distal side of the lancing device through lancing hole 176, see FIG. 4. The cantilever arms 118A and 118B have a resilient property that, when the cantilever arms are bent, a tension develops to return (or spring) the lancet 106 to its at-rest position after lancing the skin and the actuating force on the lancet 106 withdraws (e.g., the actuator rod that inserts into the port 120 withdraws). The cartridge case 104 has a port 120 on the side of the cartridge case near to the blunt end of the lancet 106 for an actuator arm or rod (e.g., a push rod) to be inserted to push the lancet, thereby extending the lancet tip out the cartridge case 104. The maximal total travel of the lancet may be a few millimeters, limited by the interference (contact) of the cantilever lancet frame 108 and cartridge wall 121. The exact limit of travel of the lancet, which is important to minimize pain and injury, may be controlled by a mechanism which pushes the cartridge frame (which will be described later in the following). Each cartridge 100 may have an identifying mark 119 on the top surface 114 or absorbent cover 110. The identifying mark 119 can indicate the number of the cartridge (in a batch) or a special function (e.g., for a calibration cartridge). Further, special function cartridges could be a different color.

FIG. 1B is a plan view of the cartridge showing the test portion 102 and the lancet structure. The test portion 102 includes a test compartment (or test area) 124 depicted as a small square. As used here, the term "test compartment" refers to a space into which blood can pass and in which the property of the blood is analyzed. A capillary passageway 126, for example, allows communication between a port (or entrance) 128 from which blood enters the test area 124. A vent hole 130 a distance (e.g., about 5 mm) away from the entrance 128 to the capillary, to the opposite side of the test area 124, terminates the capillary force to halt the filling of the capillary volume after pulling a blood sample over the active test area 124. As an alternative, a compartment without analytical capability can be used in place of a test area for storing blood. Such a compartment may have anticoagulants to prevent the blood from clotting.

In a preferred embodiment (although not clearly shown in FIGS. 1A and 1B), the test cartridge 100 has electrical contacts that allow for electrical communication with an instrument that processes (and perhaps controls) a measurement of an analyte (e.g., glucose) on the active test area. Such electrical contacts can be placed at a variety of locations on the test cartridge. Placing the contacts on the bottom (i.e., the side facing oppositely from the covering 110) permits a simple design and a simple interface to an instrument.

For analysis of the blood sampled, the test area 124 can contain chemicals that react with components of the blood samples. For example, enzymes that react with glucose can be present. The test area may also contain reagents that react with the iron present in the blood hemoglobin. Techniques, including electrochemical or spectroscopic techniques, that can be used for analysis of blood can be incorporated in the test cartridge 100. Examples of applicable analysis techniques can be found in, e.g., Tietz, Norbert W., Textbook of Chemical Chemistry, Chapter 6, pp 784–807, W. B. Saunders Co., Philadelphia, Pa., 1986, which are incorporated by reference herein. Test strips for analyzing glucose, pH, iron, and other common blood qualities are known in the art. For example, ONE TOUCH PROFILE diabetes tracking system commercially available from Lifescan Inc., Milpitas, Calif. 95035 has a unit that utilizes a strip for analyzing blood glucose and has an electronic system for displaying the result of analysis.

The top plate 112 or the top surface 110 may have a variety of useful markings that indicate which cartridge is in use (in the case that the cartridge is one out of many from a stack of cartridges), and indication of batch or lot number of manufacture (for quality control and calibration), or that the cartridge is a special-purpose cartridge (e.g., for checking or calibration).

Figure 2:
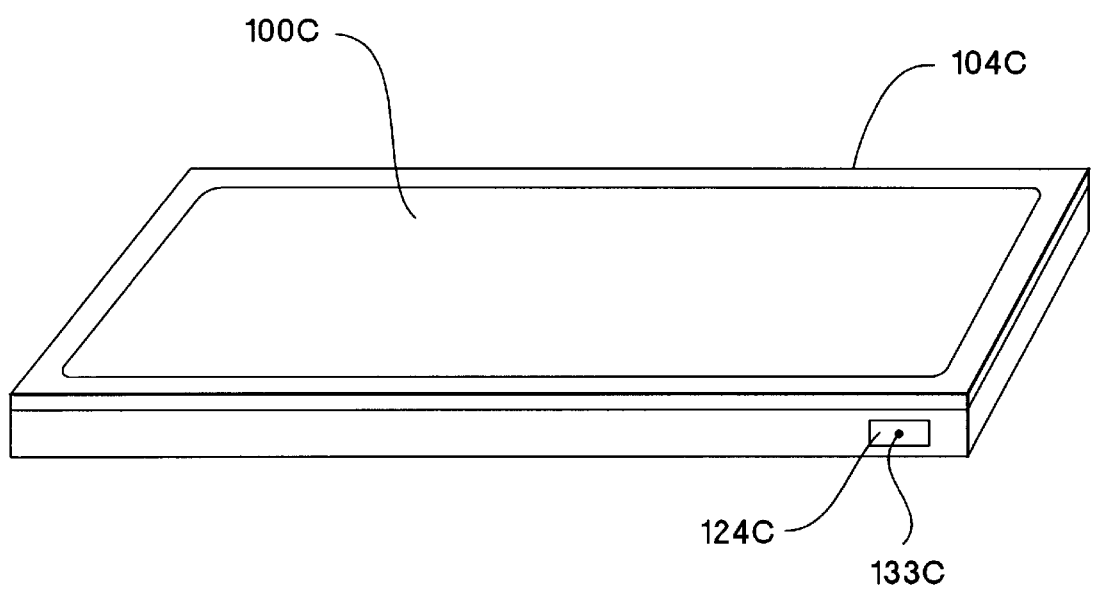
FIG. 2 shows an isometric view of another flat type test cartridge of the present invention.

Other embodiments of flat cartridges are also applicable in accordance with the present invention, such as a test cartridge with the test area 124 protruding at a different side of the lancet area, or having a test area that resides directly neighboring the lancet 106 near the tip 122, so that the entrance (i.e., sample port) 128 to the capillary volume 126 and the exit port 133 for the lancet 106 are nearly coincident. This latter design enables the patient to lance the skin, and have the sample port for the test strip co-located for immediate filling. An example of such an embodiment is shown in FIG. 2. The test cartridge 100C has a test area 124C that is at the immediate vicinity of the lancet exit port 133C, which in this embodiment is a hole. The test area 124C can be a sensing surface surrounding the lancet exit port 133C. Preferably the test area 124C is set back slightly from the distal side of the cartridge case 104C so as to avoid inadvertent contact with skin or other objects. When the skin is lanced and a drop of blood appears, the drop of blood can reach beyond the set back distance to contact the test area 124C.

BAR-SHAPED CARTRIDGES

Figure 3A:
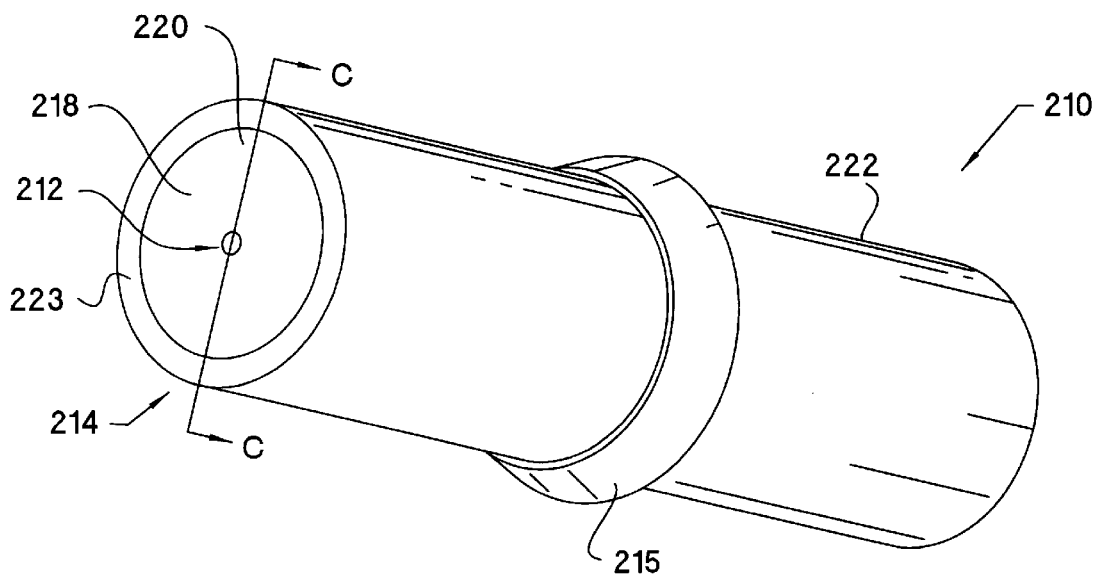
FIG. 3A shows an isometric view of a bar-shaped test cartridge of the present invention.
Figure 3B:
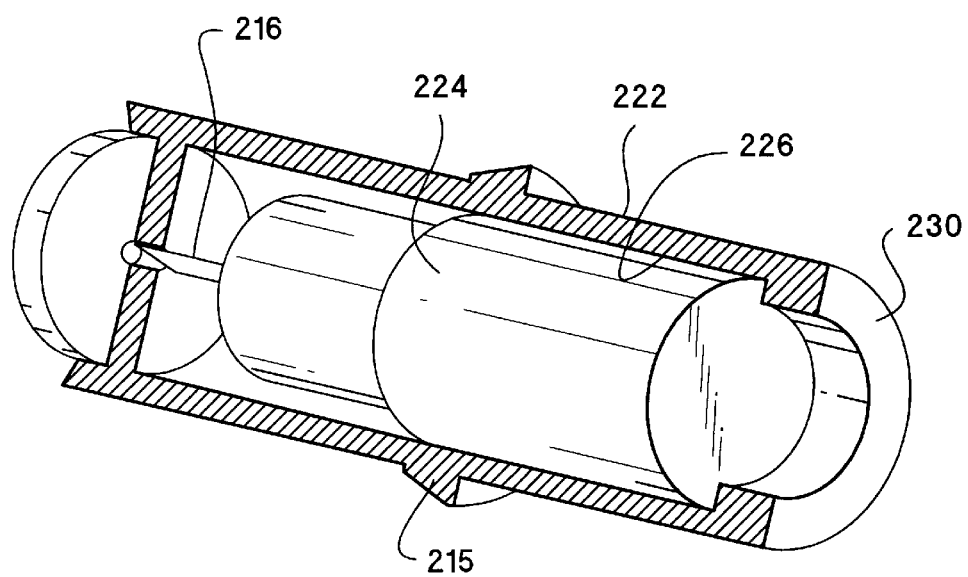
FIG. 3B shows an exploded isometric view in portion of the test cartridge of FIG. 3A.

FIGS. 3A to 3D show an embodiment of a bar-shaped test cartridge. The test cartridge has a lancet and a blood analyzer, i.e., sensor (such as a blood chemistry test strip that can determine glucose level) and can be mounted easily into a driving instrument (driver). The overall lancing device operates with the test cartridge to gather a blood sample in a single operation and simplifies the measurement procedure. FIG. 3A shows an isometric view of the embodiment of the test cartridge 210, about 6 mm in diameter and 15–20 mm in length. FIG. 3B shows an isometric view, cut-out in portion, of the test cartridge 210 along plane C—C of comparison, the size and shape is similar to that of the ULTRAFINE lancets of the Becton-Dickinson Co with a 29 AWG needle. It is noted that, although the bar-shaped test cartridge 210 has, preferably, a round cross-sectional shape, it can also have other regular cross-sectional shapes, such as oval, square, rectangle, rhombus, triangle, etc. An aperture 212 (or lancet exit hole) is located at a distal end 214 of the test cartridge 210. A lancet 216 is housed at rest inside the test cartridge 210 proximal of (i.e., beneath if considering the distal end as facing upwards) the aperture 212, which has a diameter slightly larger than the lancet 216 (~0.35 mm diameter). The lancet 216 can pass through the aperture 212 when actuated for lancing. Herein, when referred to a bar-shaped test cartridge, "top," and "up" refer to a direction or location towards the skin to be lanced, i.e., towards the distal end. The material 218 around the aperture can be an absorbent material which serves to soak up blood after lancing. The absorbent material, or the surface beneath it, can also serve as the active test area 220 for measurements of blood characteristics, such as glucose level. As in existing glucose measurement techniques, a chemical reaction occurs when blood contacts the test area 220, and thus, for example, indicates the presence and amount of glucose. The test area 220 can generate an electrical signal that is conducted from the test area 220 (preferably via conductors molded into the case) to electrical contacts (not shown) on the cartridge case 222. The test cartridge case 222 has a lip 223 protruding slightly out distally at the distal end 214. The protruding lip 223 results in a small void area protecting the test area 220 from being inadvertently touched and help to provide uniform tautness to the skin. As used herein, the meaning of the term "compartment" when referred to the space for receiving blood also can include the space encircled by the lip 223. FIG. 3B is a projected sectional view in portion of the cartridge, showing the cartridge case 222, the lancet 216, and the absorbent material 218 distal to the lancet 216 when at rest. The lancet 216 is mounted on a cylindrical lancet mount 224. The cartridge case 222 has a cylindrical internal wall 226 upon which the lancet mount 224 can slide.

Figure 3C:
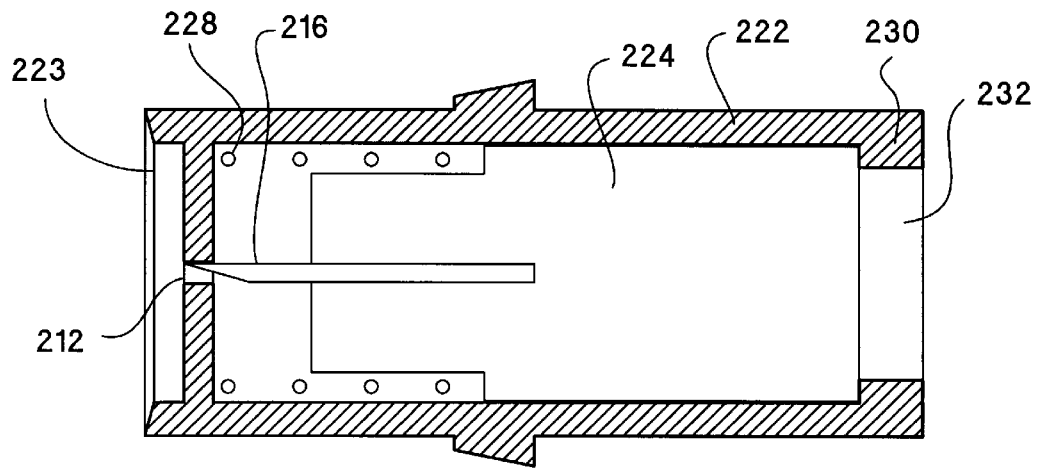
FIG. 3C shows a sectional view along the axis of the bar-shaped test cartridge of the present invention.
Figure 3D:
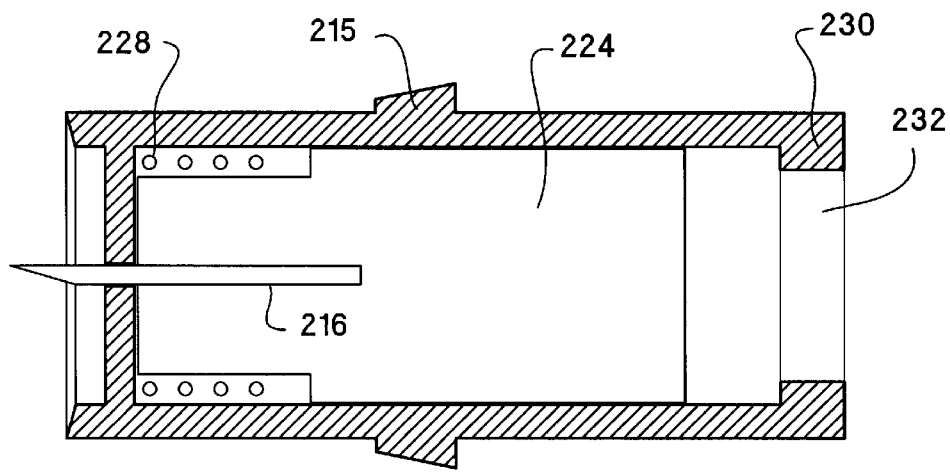
FIG. 3D shows a sectional view of the test cartridge of FIGS. 3A–3B, showing the lancet extended for lancing.

FIGS. 3C and 3D are sectional views of the test cartridge 210 along the plane C—C of FIG. 3A. Shown in FIGS. 3C and 3D (but not in FIG. 3B for clarity) is a retaining spring 228 which compresses the lancet mount 224 against the bottom 230 of the test cartridge 210. A large bore 232 on the bottom 230 of the cartridge case 222 permits an external actuator (not shown in FIGS. 3A to 3D) to extend through to act on the lancet mount 226. FIG. 3C shows the test cartridge 210 at rest, with the lancet 216 residing beneath the aperture 212 and the absorbent surface 218. When an external actuator (not shown in FIG. 3) acts through the bottom bore 232 against the lancet mount 224, the cartridge spring 228 is compressed and lancet 216 will emerge through the aperture 212 where it can pierce a patient's skin. See FIG. 3D. When the actuating force is removed, e.g., by withdrawal of the actuator, the resilient nature of the cartridge retaining spring 228 returns the lancet 216 to the at-rest position inside the cartridge case 222. In this manner, the lancet 216 is only exposed during lancing. Therefore, the user is protected against unintentionally inflicted wounds and scratches, and also from exposure to the contaminated lancet. With prior technology, accidental lancet pricks can occur more easily than with the cartridges of the present invention. It is to be understood that although test cartridges with analytical regions are described in detail herein, the lancing device of the present invention is equally applicable to cartridges that do not have an analytical region, such as a cartridge having a chamber for storing blood after sampling. Such storage cartridges, whether the flat type or the bar-shaped type, will be obvious to a person skilled in the art in view of the present disclosure. One example would be a cartridge having a storage chamber connected by a channel to the blood inlet port in the afore-mentioned test cartridges, without the reagents that can interact with the blood.

Glucometer

Figure 4:
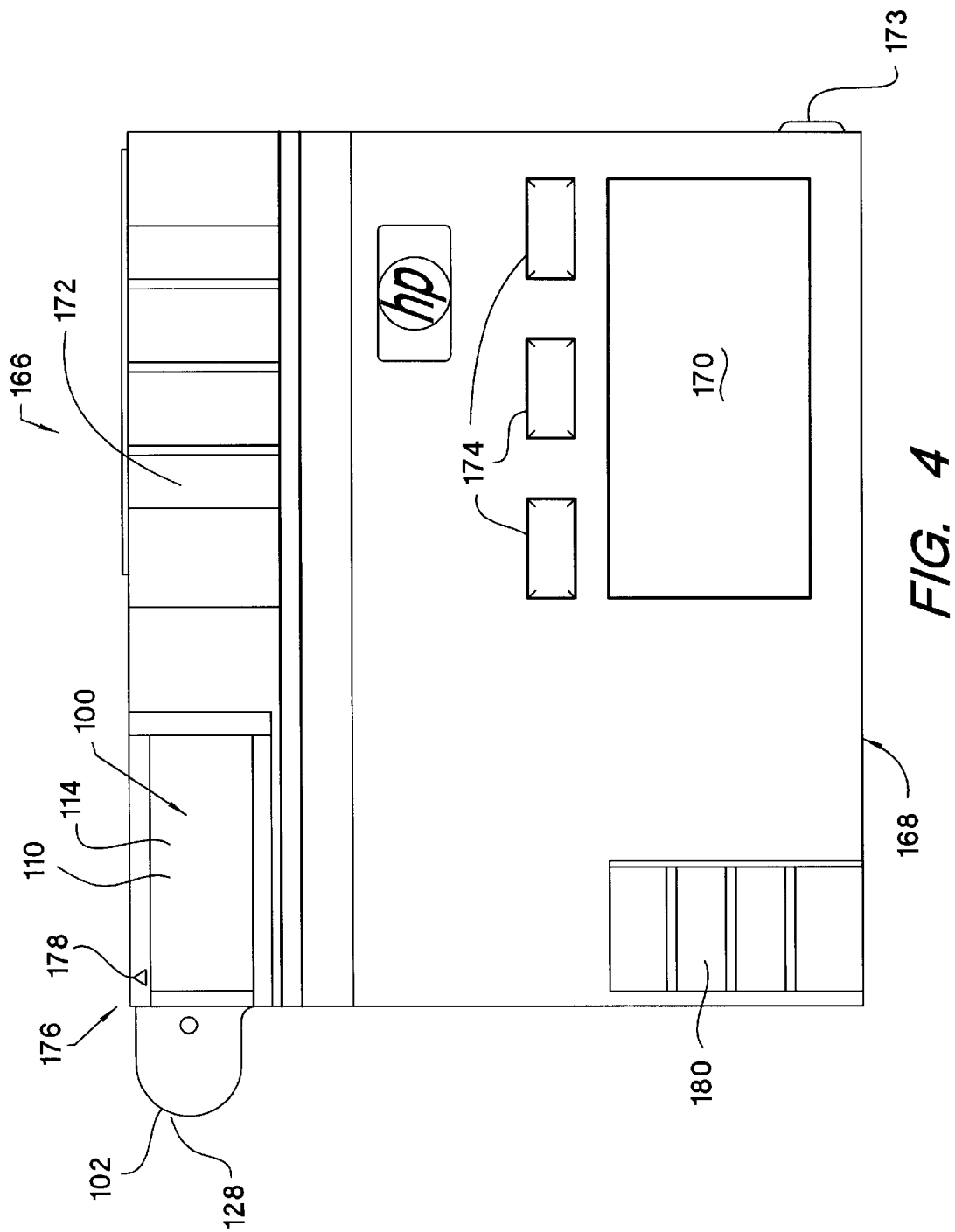
FIG. 4 shows a plan view of a glucometer of the present invention.

Lancing devices having a driver driving a cartridge can be used for lancing. FIG. 4 shows a plan view of a glucometer in which a flat cartridge of FIG. 1 has been installed (or deployed) and can be used for lancing. In this embodiment, the glucometer 166 has a body 168. A sweeper 172 in the glucometer can be used to sweep or push a single new cartridge to deploy (or load) in a position for use. After use, the sweeper 172 can be used to push the used cartridge out of the glucometer for disposal. Alternately, test cartridges may also be loaded or removed manually, e.g., using fingers.

As shown in FIG. 4, the test portion 102 (with the sample port 128 being most remote from the body 168) sticks out from the body. Additionally, preferably, the test cartridge 100 is loaded in the body of the glucometer 166 such that the test cartridge 100 has an exposed top surface 114 with an absorbent area 110 for wiping excess blood from the finger if necessary at the end of sampling and analyzing blood. Furthermore, a mark 178 can be molded or printed into the glucometer to show the location of the lancet hole 176 (corresponding to the location of the finger for lancing) through which the lancet will protrude to lance the skin of a patient.

To provide a driving (or actuating) force to push the lancet for lancing (i.e., urge the lancet forward), a cockable actuator 180, e.g., one that contains a sliding lever for cocking a spring-activated puncher (the spring and the puncher are not shown) to hold the spring in a compressed state until released, can be used. After cocking the spring in preparation for lancing, the test cartridge can be pressed against the skin site (which is to be lanced) to release the spring-activated puncher to drive the pre-loaded lancet. As a result, the lancet tip is driven to extend out of the test cartridge 100. A preferred embodiment of an actuation system for driving the lancet in a cartridge will be described later.

The body 168 of the glucometer 166 further has electronic circuits including a processor (which is not shown) to control and read the results of an analysis using the test cartridge. (A more detailed description of the instrument will follow). Analysis data and other information, e.g., date and time, can be displayed in a display 170 (e.g., LED or LCD display). The display can show the measured blood glucose concentration (e.g., in a large font for visually impaired users) and any information about the status of the measurement. On the body 168, electrical data port 173 enables electrical communication of data between the body 168 and external electronics, such as a remote computer, display unit, data storage, and the like. This data port 173 allows the transfer of data out of (or into or both) the glucometer 166, e.g., past glucose readings stored in memory. The port may also load data, programs, or information from a physician's computer. Further, electronic connections can be present in the glucometer 166 to connect electrically the processor to electrical contacts in the test cartridge to permit electrical communication, including data and instruction transmission, between the test cartridge, and the processor. Alternatively, data communication between the glucometer and a heathcare provider can be by way of wireless transmission. Control buttons 174 on the body 168 permit programming and set-up of the instrument (setting date, time, language preference, scrolling through stored values, on/off settings, instrument diagnostics, etc., as well as sending or receiving information to electronics external to the body).

To illustrate the use of the embodiment of the glucometer of FIG. 4, for example, a test cartridge 100 is loaded (or deployed) in the glucometer 166 and the spring-actuated driver is cocked to get the glucometer ready to lance a finger. When the cocked driver is released, the driver pushes the lancet to lance the finger.

A droplet of blood from the lancing wound can be exposed to sample port 128 and transferred to the test area 124 (not shown in FIG. 4) to be analyzed. Result of the analysis is transferred electrically through electrical contacts, wires, and connections to the processor. The control buttons 174 can be used to control the analysis of the blood sample, as well as to transfer information and data to external devices, e.g., computers, data storage, display, etc., through the data port 173. After analysis and data collection, the used test cartridge can be ejected.

For the flat test cartridge shown in FIG. 2, a glucometer similar to that shown in FIG. 4 can be used. Generally, that glucometer would have the same features as that of FIG. 4. When a flat test cartridge of FIGS. 2A and 2B is installed in the glucometer, the glucometer with the test cartridge would look like that of FIG. 4 except for the absence of the test portion 102 shown in FIG. 4. In the case of the test cartridge of FIG. 2, the test area 124C for receiving and analyzing blood is at the lancet exit port 133C.

Figure 7A:
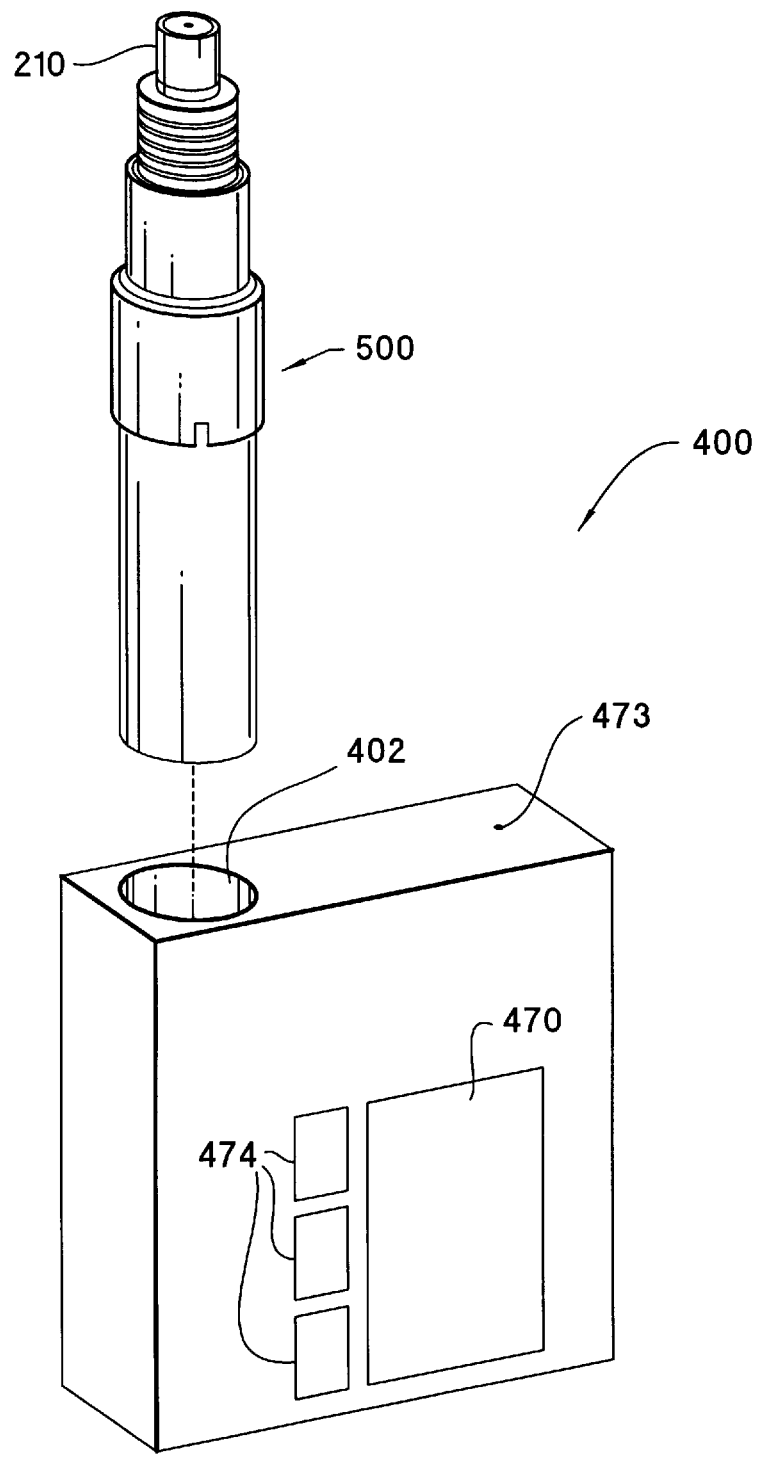
FIG. 7A shows an isometric view exploded in part, of a glucometer for a bar-shaped test cartridge.
Figure 7B:
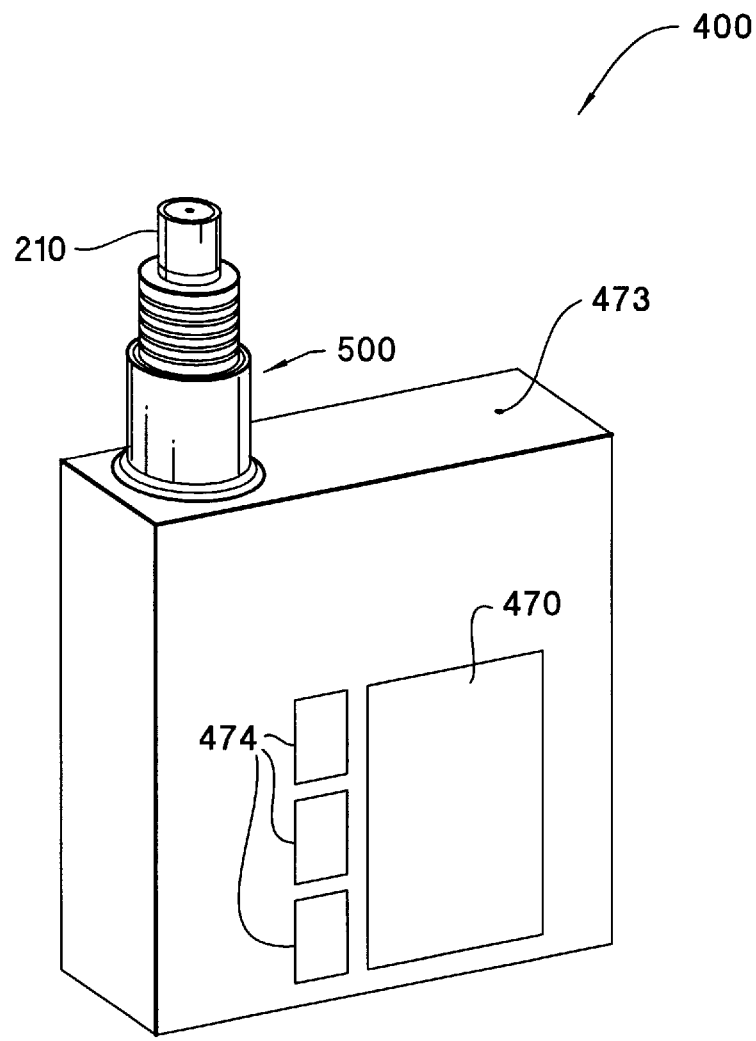
FIG. 7B shows an isometric view of the glucometer of FIG. 7A.

A glucometer for use with a bar-shaped test cartridge can have driving mechanisms, data processing electronics, as well as display and control systems similar to those for the flat type test cartridges. An embodiment of a glucometer suitable for use with a bar-shaped test cartridge of FIGS. 3A–3D is shown in FIG. 7A and FIG. 7B, which will be described later. An embodiment for the driving mechanism that enables reproducible lancing using a bar-shaped cartridge is shown in FIGS. 5A and 5B.

DEVICE FOR REPRODUCIBLE LANCING

In the embodiment shown in FIGS. 5A and 5B, the lancing device has a generally elongated shape. FIGS. 5A and 5B show sectional views of the lancing device along the elongated dimension. The sectional views are sections through different angles (right angle to each other), so that they reveal different aspects of the interior parts. FIG. 5C is a schematic representation of the cross-section of the lancing device, showing line A—A as the plane for the sectional view of FIGS. 5A and line B—B as the plane for the sectional view of FIG. 5B. This lancing device embodiment permits adjustment of the depth of the lancet and adjustment of the preload applied to the skin before lancing. In FIGS. 5A and 5B, the test cartridge 210 is shown removed from the lancing device 500 for clarity.

The lancing device 500 has a cartridge holder 502 with a recessed section 506 that accepts a bar-shaped test cartridge 210, similar to the bar-shaped test cartridge of FIG. 2A and FIG. 2B. The test cartridge 210 can be mounted in the cartridge holder 502 in a highly reproducible manner. That is, the test cartridge 210 can be repeatedly mounted and removed from the cartridge holder 502 and still attain the same position relative to the cartridge—by locating against a cartridge flange 215 that is molded onto the case 222 of the test cartridge 210. The bore 232 in the bottom of the test cartridge 210 is exposed to the interior of the lancing device through a bore 510 in the cartridge holder 502.

If the test cartridge 210 has an active test area for analytical measurement, then the test cartridge 210 should preferably also possess electrical contacts 519, which communicate to complementary contacts 523 in the cartridge holder 502. The lancing device 500 can either contain a processor such as CPU of a computer (not shown) or communicates with a CPU that can compute results from the signals received from the test cartridge. Thus, the lancing device 500 becomes part of an entire measurement instrument, which can compute and display results (such as blood glucose concentration).

The cartridge holder 502 can slide freely inside a casing 526. A force adjuster 528 can also slide freely inside the casing 526. The force adjuster 528 has a threaded end 530 that threads into matching threads on the cartridge holder 502. An adjuster spring 532 is compressed between the cartridge holder 502 and a flange 534 on the casing 526. By adjusting the position of the threaded end 530 of the force adjuster 528 relative to the threads on the cartridge holder 502, the degree of compression of the adjuster spring 532 can be adjusted, to apply an outward force on the cartridge holder 502 (and thereby also the force adjuster to which the cartridge holder is threaded). An adjuster flange 536 on the force adjuster 528 restrains the travel of the force adjuster (and cartridge holder 502) relative to the casing 526. Protruding further from the adjuster flange 536 on the force adjuster 528 is a trigger 538, which extends to within a preset distance of a catch 540 on the casing 526 (see FIG. 5B). Inside the casing 526 is a plunger 542 having a larger base 544 and a long, more slender shaft 546. The base 544 has a small recession 548 and two protruding tabs 550. Attached to the plunger base 544 is a driving spring 552 which extends inside the casing 526 to the casing base 554. In equilibrium, the driving spring 552 holds the plunger 542 in the location shown in FIG. 4A (inside the casing) with the tip 556 of the plunger long shaft 546 held at a preset location inside the bore 510 of the cartridge holder 502. Around the casing 526 is a depth adjuster 560 and a cocking tube 562. One end of the cocking tube 562 has threads 564 that match to the threads in the depth adjuster 560. Between the casing 526 and the cocking tube 562 (more specifically between the casing base 554 and the tube flange 566) is a tube spring 568 which applies a compressive force between the casing base 554 and the tube flange 566 on the cocking tube 562. The base (or closed end) 570 on the end of the cocking tube remote from the test cartridge 210 restrains the cocking tube 562 against the casing base 554.

FIGS. 6A to 6F illustrate the general steps of lancing with the lancing device of FIGS. 5A and 5B. These steps are described as follows. In FIGS. 6A to 6F, for the sake of clarity, the locations of the driving spring 552, cocking tube spring 568, and adjuster spring 532 are indicated, but these springs are not drawn.

Figure 6A:
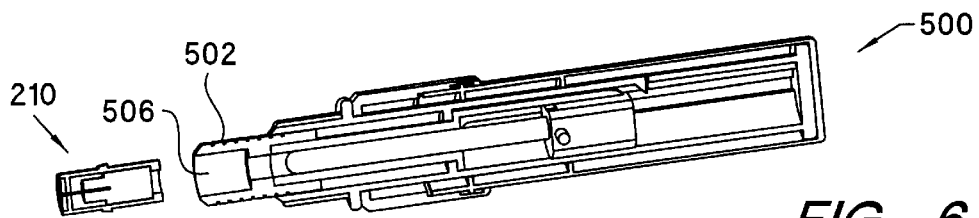
FIGS. 6A to 6F show the process of using the blood sampling device of FIGS. 5A to 5C for lancing and sampling blood.
Figure 6B:
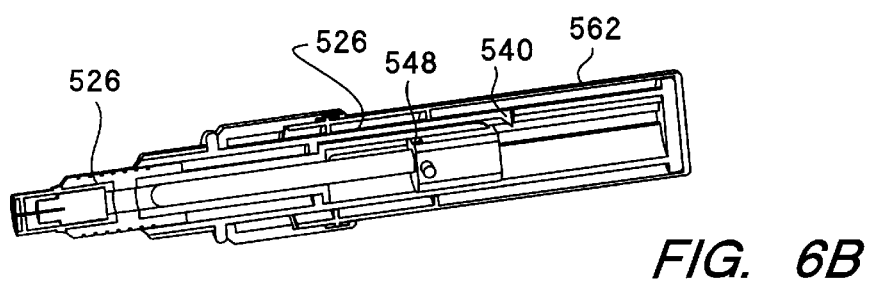

1. Load a test cartridge 210 in the cartridge holder 502 (FIGS. 6A and 6B).

Figure 6C:
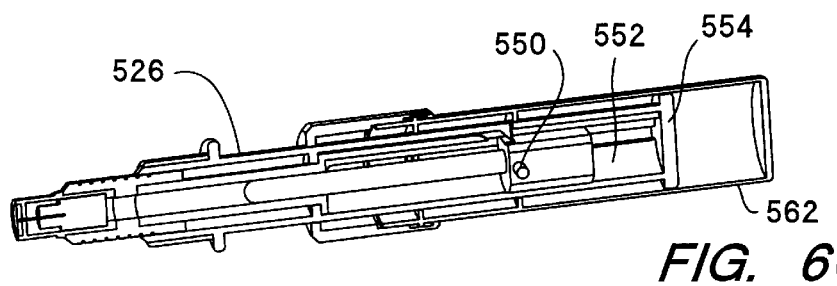

2. Cock the lancing device 500 by pulling the cocking tube 562 back until the catch 540 on the casing 526 locks into the recession 548 on the plunger 546, thereby preloading (compressing) the driving spring (at location 552, but not shown in FIG. 6) against the base 554 of the casing 526 (FIG. 6C). When the cocking tube 562 is pulled in the proximal direction (away from the test cartridge 210), a cocking tube distal flange 572 (see FIG. 5A for structural details of the lancing device) pushes on the protruding tabs 550 of the plunger 542, thereby pushing the plunger 546 to compress the driving spring 552.

Figure 6D:
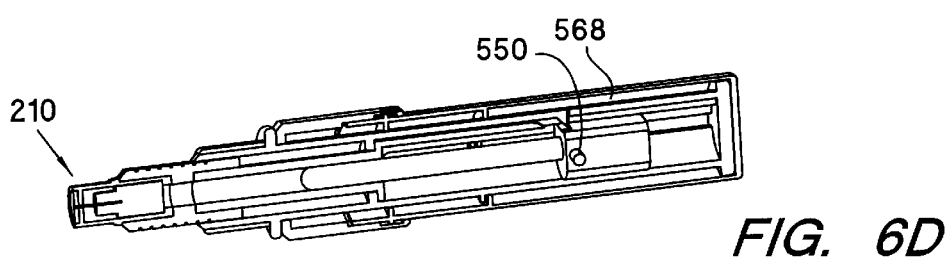

3. Release the cocking tube 562, thus allowing the force from the compressed cocking tube spring 568 to return the cocking tube 562 to its earlier resting position (FIG. 6D).

Figure 6E:
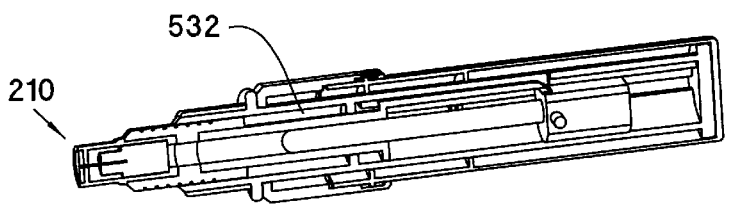

4. Touch the intended site for lancing on the skin to the test cartridge 210 at its distal end. Continue to press the test cartridge 210 against the skin by pushing the entire lancing device 500. As a result, the cartridge holder 502 is compressed partially into the lancing device 500 against the force of the adjuster spring 532 (FIG. 6E). At the same time the trigger 538 advances toward the catch 540 which retains the plunger 542.

Figure 6F:
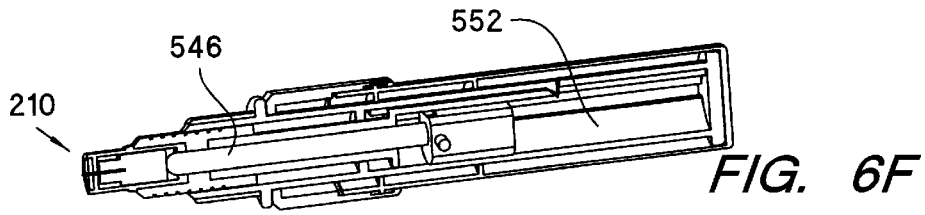

5. At a predetermined location the trigger 538 releases the catch 540 from the plunger 542 and the driving spring 552 drives the plunger 542 distally, thereby driving the lancet of the test cartridge into the skin (FIG. 6F). Afterwards, in the preferred mode in which the driving spring 552 is a ballistic spring that attaches to the plunger base 544, the driving spring recoils to its resting position and pulls back the plunger (as in FIG. 6B). As a result, the lancet retracts from the skin by the spring 228 in the test cartridge 210.

The electrical contacts in the test cartridge 210 are in electrical communication with the electronics of the lancing device 500, which in turn is in electrical communication with electrical circuits, processors, displays, and the like that is applicable for analyzing, processing, or displaying of the results of analysis of blood in the test area. If preferred, such electronics, circuits, processors, and display can be incorporated in the lancing device 500 itself.

In order to adjust the preload (which affects the skin tension), the user can rotate the cartridge holder 502 with respect to the casing 526, which causes it to move along the matching threads of the force adjuster 528. Varying the position of the cartridge holder 502 with respect to the force adjuster 528 varies the compression of spring 532. The user can increase or decrease the force on the cartridge holder 502, thereby setting the force required to push the trigger 538 to reach the catch 540 on the plunger 542. That required force is the preload force at the instant of lancing.

In order to further adjust the depth of penetration of the lancet, the user rotates the depth adjuster 560, causing the cocking tube 562 to slide into a new position where it remains fixed with respect to the depth adjuster 560. The location of the cocking tube 562 determines the location of flange 572 on the cocking tube. Flange 572 acts as a limiting stop for the travel of the plunger 542 inside the casing. The lancet 216 can only travel the distance that the plunger pushes it, so setting the limit of travel of the plunger 542 determines how far the lancet 216 can extend out of the test cartridge 210. This is the maximum depth of penetration of lancing.

The users of the lancing devices of the present invention can vary the settings in the lancing device to determine the best settings for their own use. Typically, users would set the lancet to (1) minimize the pain, (2) reduce the size of the wound, and (3) produce the amount of blood sample they need for measurement. The design of this device permits a user to control the preload and depth of penetration to the desired settings for optimal blood sampling and pain level. Once the optimal setting is achieved, the lancing device can be used repeatedly by the same user without the need for frequent adjustment.

FIG. 7A is a partially exploded view and FIG. 7B is an isometric projected view showing a glucometer 400 having a lancing device 500 like that described above. The lancing device 500 is inserted into a receptacle bore 402 which can hold the lancing device tightly, for example, by threads or interlocking pins and notches, clips, screws, and the like. Electrical contacts in the body of the glucometer 400 and the lancing device 500 provide electrical communication such that information can be transferred between them. The glucometer 400, similar to the glucometer in FIG. 4, can have control buttons 474, display 470, as well as data port 473 for communication with an external device such as a computer or a doctor's remote monitoring system.

Figure 8A:
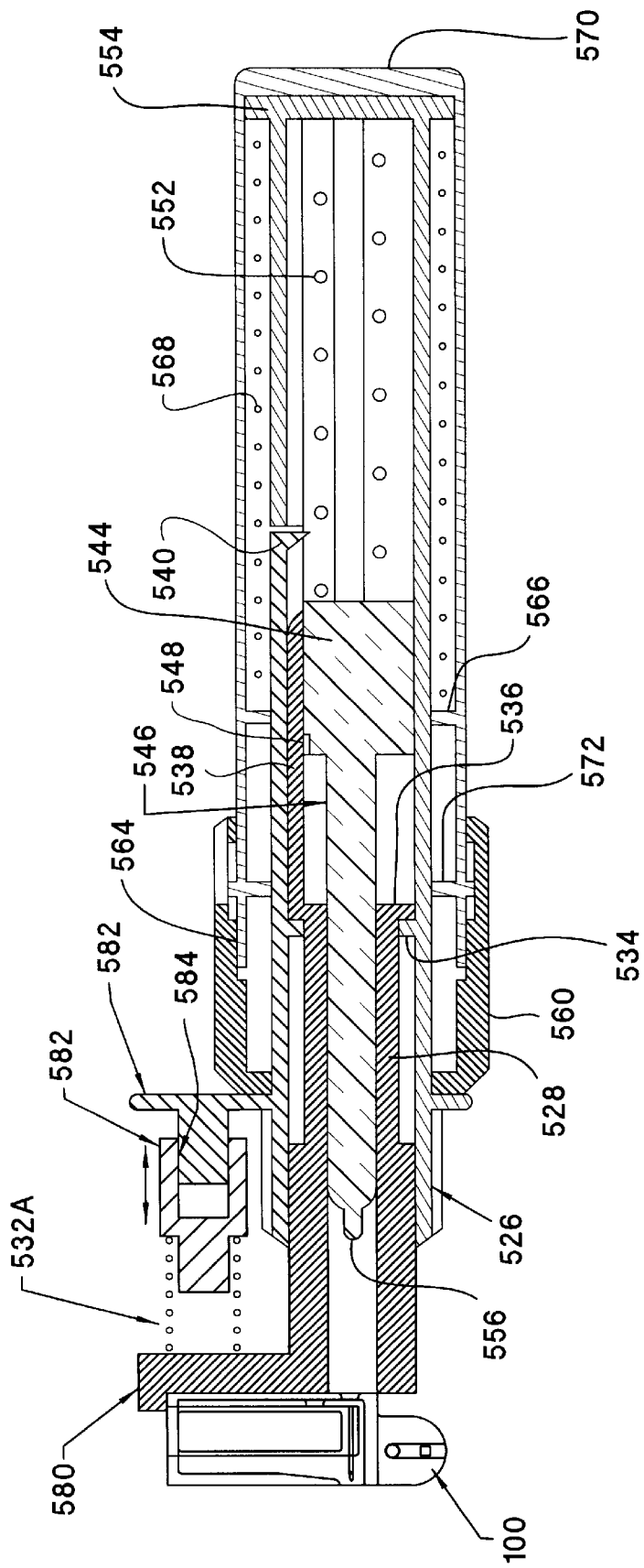
FIGS. 8A shows a sectional view in portion of an embodiment of a blood sampling device with a flat test cartridges.
Figure 8B:
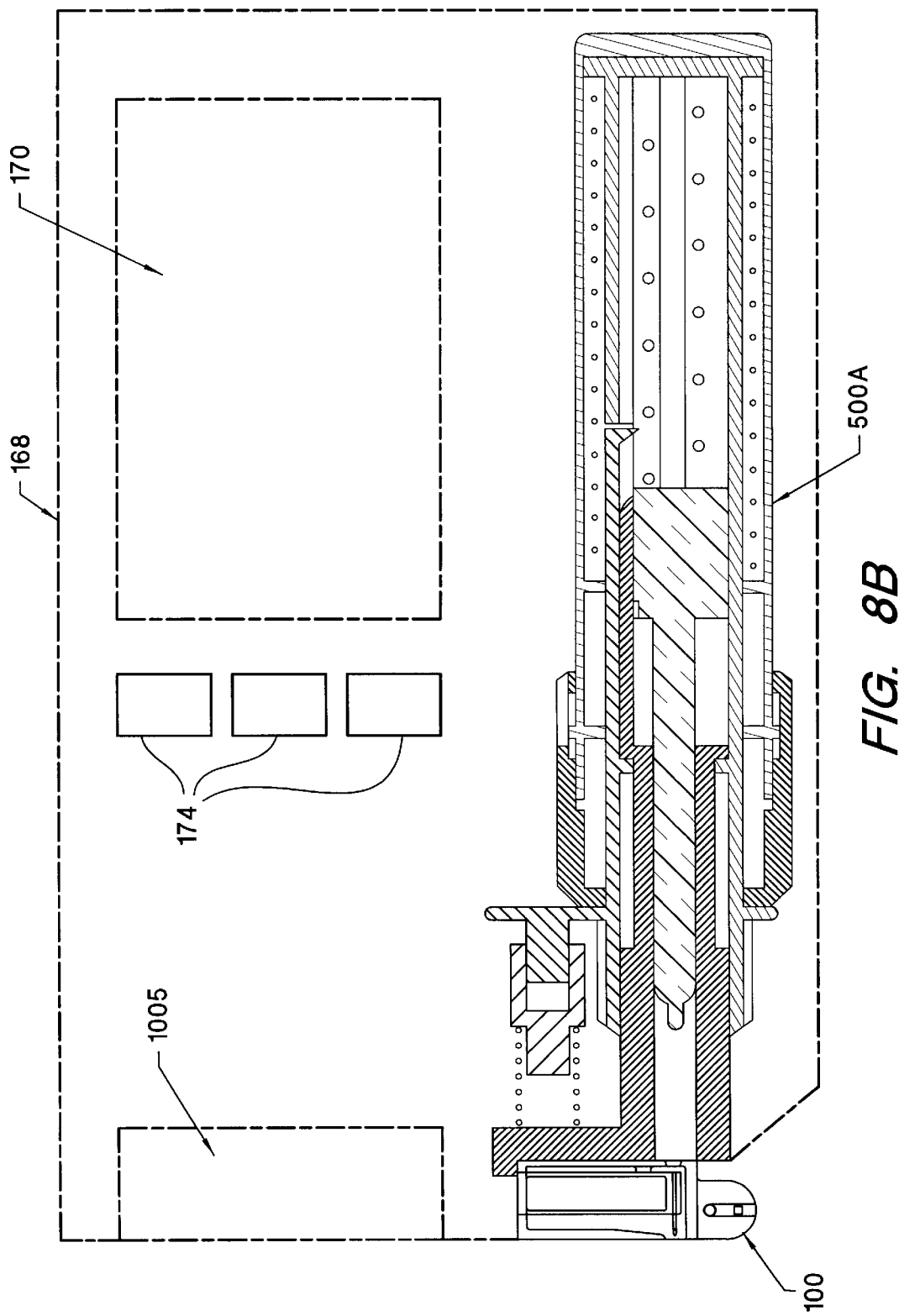
FIGS. 8B shows an schematic view of an embodiment of a glucometer having the blood sampling device of FIG. 8A.

The driver mechanism for driving the lancing device of FIGS. 5–6 can also be adapted to be used for driving the flat test cartridge in the glucometer shown in FIG. 4. FIG. 8A shows such a lancing device that can provide reproducible lancing. Generally, this lancing device 500A has features similar to those of FIGS. 5 and 6 including, a casing 526A, force adjuster 586, flange 534, preload adjuster spring 532A, adjuster flange 536, trigger 538, catch 540, plunger 542 having a larger base 544 and a long, more slender shaft 546, small recession 548, protruding tabs 550, driving spring 552, casing base 554, tip 556, depth adjuster 560, cocking tube 562, tube spring 568, and tube base (or closed end) 570. However, because of the difference in shape between the flat and the bar-shaped test cartridges, in FIG. 8A, the cartridge holder 502A can have guard ridges (not shown) on a mount 580 that restrains the test cartridge 100 so that the test cartridge can be slid into position and that the cartridge case will not be moved distally when the plunger 542 pushes the lancet distally. The casing 526 has an elbow 582 with threads 584 matched to a preload adjuster 586 for adjusting the preload force resulting from the preload adjuster spring 532A compressing on the mount 580. FIG. 8B shows a way the driving mechanism of FIG. 7A can be oriented to relate to display 170 and buttons 174 of a glucometer similar to that of FIG. 4. The figure shows a spare test cartridge 100S which can be swept into position after the test cartridge 100 has been used and ejected.

In the embodiment shown in FIGS. 1A and 1B, the test cartridge has a generally thin and flat shape. The thin, flat design of the cartridges permits several cartridges to be packaged (in a stack) in a small cassette-like container, similar in design to existing dispensers of single-edged razor blades. Furthermore, cassettes of bar-shaped test cartridges can also be made. Such cassettes can be incorporated into the glucometers disclosed herein with only slight modifications to result in reproducible lancing apparatuses. Details of a few embodiments of cassettes are disclosed in copending application Docket No. 10970749-1, entitled "Cassette of Lancet Cartridges for Sampling Blood," filed on the same day and commonly assigned to the same assignee as the present application. Said copending applications are incorporated by reference in their entirety herein.

To illustrate the use of the embodiments of the glucometers for example, a test cartridge is loaded (or deployed) in the glucometer and the spring-actuated driver is cocked to get the glucometer ready to lance a finger. When the cocked driver is released, the driver pushes the lancet to lance the finger. After a lancet has pierced the lateral edge of a finger successfully, a convenient way to educe blood from the wound site is to press gently on the fingertip near the wound where the tissue is soft. A gentle push for a second will promote a few microliters of blood to appear as a stationary droplet (to get a droplet of a 2–20 $\mu l$, which is a sufficient sample for glucose measurements).

The droplet of blood can be exposed to sample port and transferred to the test area of the test cartridge to be analyzed. Result of the analysis is transferred electrically through electrical contacts, wires, and connections to the processor in the glucometer or to external terminals.

Details of lancing devices and glucometers suitable for using test cartridges for lancing is disclosed in the copending U.S. patent application Docket No. 10970322-1, entitled "Integrated System and Method for Sampling Blood and Analysis" filed on the same day and commonly assigned to the same assignee as the present application, said copending application is incorporated by reference in its entirely herein.

Although the preferred embodiment of the present invention has been described and illustrated in detail, it is to be understood that a person skilled in the art can make modifications, especially in size and shapes of features within the scope of the invention. For example, instead of matching screw threads for adjusting the relative position of parts, other position-adjusting mechanisms such as pins in locking notches, clips, set screws, and the like can be used. In another example, it is contemplated that the body of a lancing device of FIG. 5 can include electronics and displays for analyzing, organizing, and displaying the information generated by the test area in the test cartridge.

What is claimed is:

1. A lancing apparatus for obtaining blood for analysis from the skin of a patient with a controlled degree of lancing, comprising:

(a) a cartridge which comprises a cartridge case having a lancing opening and a lancet having a tip, the lancet operatively connected to the cartridge case to allow the lancet to protrude through the lancing opening and move the tip towards the skin for lancing to yield blood; and (b) a driver for driving the lancet to move the tip distally to lance the skin, the driver being triggerable by said skin exerting a force against the apparatus when said force exceeds a preset amount of preload force; wherein a spring generates a preload force which needs to be overcome to actuate the driver to drive the lancet towards the skin, the spring resting against an adjuster for adjusting the compression of the spring to vary the preload force.

2. The apparatus according to claim 1 wherein the driver is adjustable to vary the protrusion of the lancet into the skin in lancing.

3. The apparatus according to claim 2 wherein the driver has parts with matching screw threads to adjust the protrusion length of the lancet out of the lancing opening.

4. The apparatus according to claim 1 wherein the cartridge is detachably held in said apparatus such that the cartridge can be removed after obtaining blood from the skin.

5. The apparatus according to claim 1 further comprising, associated with the cartridge case a compartment for receiving blood.

6. The apparatus according to claim 5 comprising, associated with the cartridge case an analytical region for analyzing the property of blood.

7. The apparatus according to claim 6 wherein the analytical region is near the lancing opening for fluid communication between the analytical region and the opening.

8. The apparatus according to claim 6 wherein the analytical region is located distal to the lancet tip before the lancet is extended through the opening.

9. The apparatus according to claim 6 wherein the analytical region encircles the lancing opening on the exterior of the cartridge case.

10. The apparatus according to claim 6 further comprising a display for displaying the analysis result.

11. The apparatus according to claim 1 wherein the cartridge includes two surfaces on opposite sides to facilitate stacking cartridges together such that one cartridge can be transferred from a stack of cartridges to be associated with the driver while the other cartridges in the stack are retained on the stack.

12. The apparatus according to claim 1 wherein the cartridge is bar-shaped having a longitudinal axis parallel to which the lancet can extend to lance the skin.

13. The apparatus according to claim 1 further comprising:

a housing having the driver for causing the lancet to extend the lancet tip outside the cartridge case, the cartridge being detachably held in said housing such that the cartridge can be removed after obtaining blood.

14. A method for sampling blood from the skin of a patient, comprising:

(a) providing an apparatus having a lancet which has a tip shielded in the apparatus;

(b) adjusting a preload force in the apparatus which needs to be overcome to drive the lancet towards the skin; and (c) pushing the skin against the apparatus, thereby triggering the apparatus to drive the lancet to extend the lancet tip out of the apparatus when a preset preload force is exceeded.

15. The method according to claim 14 further comprising adjusting the apparatus to vary the depth of protrusion by the lancet into the skin.

16. The method according to claim 14 further comprising extending the lancet through a cartridge which shields the lancet before triggering the apparatus.

17. The method according to claim 16 further comprising receiving blood from lancing in a compartment associated with the cartridge case.

18. The method according to claim 16 further comprising allowing blood from the lanced skin to contact an analytical region associated with the cartridge for analysis.

19. A lancing apparatus for sampling and analyzing blood from the skin of a patient, comprising:

(a) a cartridge having
      (i) a cartridge case having a lancing opening through which a lancet can protrude and having a sample compartment near the lancing opening;
      (ii) a lancet housed in the cartridge case and operatively connected thereto such that it is drivable to extend through the lancing opening for lancing the skin to yield blood; and (b) a housing having a driver for driving the lancet to extend the lancet through the lancing opening, the cartridge being detachably held in said housing such that the cartridge can be removed after sampling blood, the driver having a cocking position which is triggerable when the skin to be lanced exerts on the driver a force exceeding a preset force to release from the cocking position, thereby urging the lancet toward the skin.

20. The apparatus according to claim 19 further comprising an analytical region associated with the cartridge case for analysis of blood.

21. A lancing apparatus for obtaining blood for analysis from the skin of a patient with a controlled degree of lancing, comprising:

(a) a cartridge which comprises a cartridge case having a lancing opening and a lancet having a tip, the lancet operatively connected to the cartridge case to allow the lancet to protrude through the lancing opening and move the tip towards the skin for lancing to yield blood; and (b) a driver for driving the lancet to move the tip distally to lance the skin, the driver being triggerable by said skin exerting a force against the apparatus when said force exceeds a preset amount of preload force; wherein the driver has movable parts to adjust the protrusion length of the lancet out of the lancing opening.

* * * * *

(12) EX PARTE REEXAMINATION CERTIFICATE (5835th)
United States Patent
Simons et al.

(10) Number: US 5,871,494 C1
(45) Certificate Issued: Jul. 31, 2007

(54) REPRODUCIBLE LANCING FOR SAMPLING BLOOD

(75) Inventors: Tad Decatur Simons, Palo Alto, CA (US); Michael Greenstein, Los Altos, CA (US); Dominique Freeman, Cabrillo Hwy., CA (US); Leslie Anne Leonard, Portolla Valley, CA (US); David A. King, Menlo Park, CA (US); Paul Lum, Los Altos, CA (US)

(73) Assignee: Hewlett-Packard Company, Palo Alto, CA (US)

Reexamination Request:
No. 90/005,478, Sep. 7, 1999

Reexamination Certificate for:
Patent No.: 5,871,494
Issued: Feb. 16, 1999
Appl. No.: 08/985,303
Filed: Dec. 4, 1997

(51) Int. Cl.
*A61B 17/14* (2006.01)
*A61B 5/15* (2006.01)

(52) U.S. Cl. .................. 606/181; 606/182; 606/183; 606/184; 606/186; 604/137; 604/157

(58) Field of Classification Search ......... 606/181–186, 606/167; 604/137, 157
See application file for complete search history.

(56) References Cited

U.S. PATENT DOCUMENTS

| 3,494,358 A | 2/1970 | Fehlis et al. | 128/218 |
| 4,637,403 A | 1/1987 | Garcia et al. | 128/770 |
| 5,279,294 A | 1/1994 | Anderson et al. | 128/633 |
| 5,730,753 A | 3/1998 | Morita et al. | 606/181 |
| 5,879,311 A | 3/1999 | Duchon et al. | 600/583 |

FOREIGN PATENT DOCUMENTS

| DE | 4212315 A1 | 10/1993 |
| WO | WO93/09723 | 5/1993 |
| WO | WO97/42882 | 11/1997 |

*Primary Examiner*—Vy Q. Bui

(57) ABSTRACT

A blood analysis apparatus for obtaining blood for analysis from the skin of a patient with a controlled degree of lancing. The apparatus including a cartridge and a driver. The cartridge includes a cartridge case and a lancet. The lancet has a tip and is housed in the cartridge case. The lancet can be driven to extend the tip outside the cartridge case through an opening for lancing the skin of the patient to yield blood. The driver drives the lancet to move the tip distally to lance the skin. The driver is triggerable by the skin which is to be lanced exerting a force exceeding a preset amount against the triggering mechanism of the apparatus, to drive the lancet toward the skin.

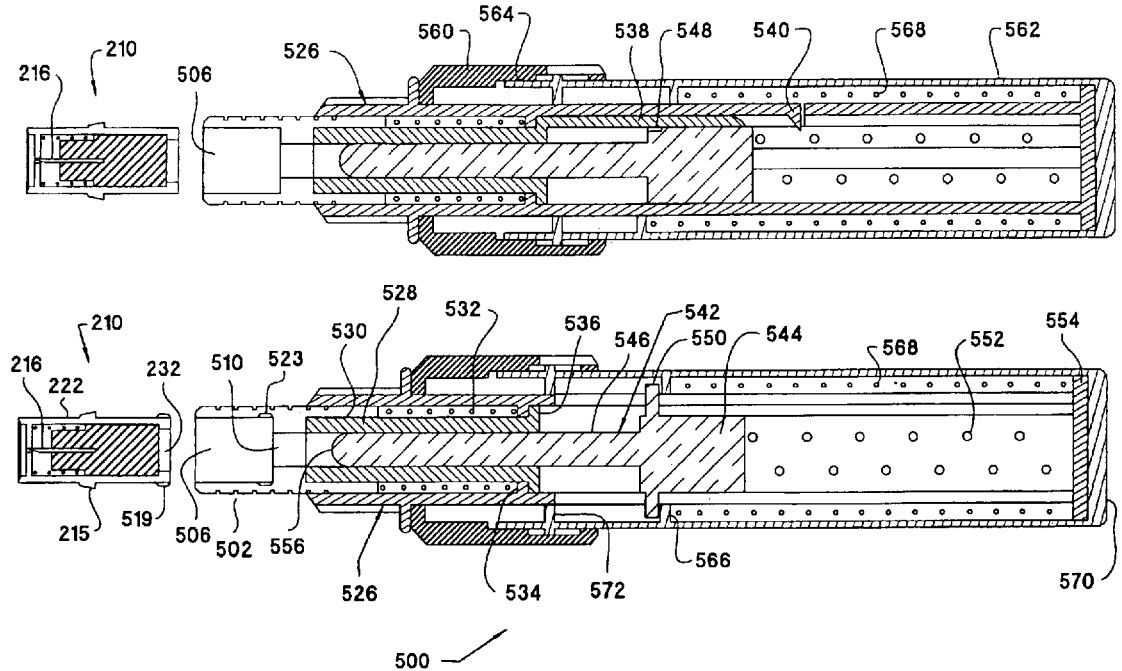

US 5,871,494 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 14, 16, 19 and 21 are determined to be patentable as amended.

Claims 2–13, 15, 17, 18 and 20 dependent on an amended claim, are determined to be patentable.

New claims 22–26 are added and determined to be patentable.

1. A lancing apparatus for obtaining blood for analysis from the skin of a patient with a controlled degree of lancing, comprising:
   (a) a cartridge which comprises a cartridge case having a lancing opening and a lancet having a tip, the lancet operatively connected to the cartridge case to allow the lancet to protrude through the lancing opening and move the tip towards the skin for lancing to yield blood; and
   (b) a driver *including*
      (*i*) *a drive mechanism* for driving the lancet to move the tip distally to lance the skin[.];
      (*ii*) *a trigger operatively coupled to the drive mechanism,* the [driver] *trigger* being triggerable by said skin exerting a force against *a portion of* the *lancing* apparatus *contacting skin near an intended site for lancing* when [said] *the* force exceeds a [preset amount of] preload force;
      (*iii*) [wherein a] *an adjuster* spring [generates a]*operatively coupled to the trigger, the adjuster spring providing the* preload force [which needs to be overcome to actuate the driver to drive the lancet towards the skin, the spring resting against]*; and*
      (*iv*) an adjuster [for adjusting] *resting against the adjuster spring, the adjuster operating to adjust* the compression of the *adjuster* spring to vary the preload force.

14. A method for sampling blood from the skin of a patient, comprising:
   (a) providing an apparatus having *a drive mechanism to drive* a lancet [which has a] tip [shielded in the apparatus] *through a lancing aperture to penetrate the skin*;
   (b) adjusting a preload force in the apparatus[which]*, provided in addition to a lancet driving force provided by the drive mechanism, wherein the preload force* needs to be overcome to drive the lancet towards the skin; and
   (c) pushing the skin against *a portion of* the apparatus *defining the lancing aperture,* thereby triggering the apparatus to drive the lancet to extend the lancet tip out of the apparatus when [a preset] *the* preload force is exceeded.

16. The method according to claim 14 further comprising *adjusting the depth of protrusion by the lancet into the skin and* extending the lancet through a cartridge which shields the lancet before triggering the apparatus.

19. A lancing apparatus for sampling and analyzing blood from the skin of a patient, comprising:
   (a) a cartridge having
      (i) a cartridge case having a lancing opening through which a lancet can protrude and having a sample compartment near the lancing opening;
      (ii) a lancet housed in the cartridge case and operatively connected thereto such that it is drivable to extend through the lancing opening for lancing the skin to yield blood; and
   (b) a housing having a driver for driving the lancet to extend the lancet through the lancing opening, the cartridge being detachably held in said housing such that the cartridge can be removed after sampling blood, the driver having a cocking position which is triggerable when the skin to be lanced exerts on [the driver] *a portion of the apparatus contacting skin surface having an intended site for lancing* a force exceeding [a] *an adjustable* preset force to release from the cocking position, thereby urging the lancet toward the skin.

21. A lancing apparatus for obtaining blood for analysis from the skin of a patient with a controlled degree of lancing, comprising:
   (a) a cartridge which comprises a cartridge case having a lancing opening and a lancet having a tip, the lancet operatively connected to the cartridge case to allow the lancet to protrude through the lancing opening and move the tip towards the skin for lancing to yield blood; and
   (b) a driver for driving the lancet to move the tip distally to lance the skin, the driver being triggerable by said skin exerting a force against the apparatus when said force exceeds a preset amount of preload force; wherein the driver has movable parts to adjust the protrusion length of the lancet out of the lancing opening *and the apparatus having an adjuster resting against an adjuster spring, the adjuster operating to adjust the compression of the adjuster spring to vary the preload force*.

*22. The apparatus according to claim 1 wherein the drive mechanism comprises a driving spring.*

*23. The apparatus according to claim 2 wherein the cartridge can be removed from the driver without disassembling any part of the apparatus except the removal of the cartridge from the driver.*

*24. The method according to claim 14 further comprising coupling a cartridge, which includes the lancet, with a driver for driving the lancet such that the apparatus is ready for lancing without disassembling any part of the driver.*

*25. The method according to claim 14 wherein the drive mechanism comprises a driving spring and the preload force is provided by an adjuster spring.*

*26. A method for sampling blood from the skin of a patient, comprising:*
   *(a) providing an apparatus having a drive mechanism to drive a lancet tip of a lancet through a lancing aperture to penetrate the skin;*

(b) using an adjuster resting against an adjuster spring to adjust a preload force in the apparatus, provided in addition to a lancet driving force provided by the drive mechanism, wherein the preload force needs to be overcome to drive the lancet towards the skin;

(c) adjusting a movable part on the apparatus to adjust a protrusion length of the lancet out of the lancing aperture; and (d) pushing the skin against the apparatus, thereby triggering the apparatus to drive the lancet to extend the lancet tip out of the apparatus when the preload force is exceeded.

\* \* \* \* \*